United States Patent [19]

McConnell

[11] Patent Number: 4,490,216

[45] Date of Patent: Dec. 25, 1984

[54] LIPID MEMBRANE ELECTROANALYTICAL ELEMENTS AND METHOD OF ANALYSIS THEREWITH

[75] Inventor: Harden M. McConnell, Stanford, Calif.

[73] Assignee: Molecular Devices Corporation, Palo Alto, Calif.

[21] Appl. No.: 570,063

[22] Filed: Jan. 12, 1984

Related U.S. Application Data

[63] Continuation-in-part of Ser. No. 463,577, Feb. 3, 1983, abandoned.

[51] Int. Cl.[3] .............................................. C12Q 1/00
[52] U.S. Cl. ................................... 204/1 T; 204/403; 357/25; 435/817
[58] Field of Search ....................... 357/25; 324/71.6; 204/403, 1 T, 1 E; 435/817

[56] References Cited

U.S. PATENT DOCUMENTS

| | | | |
|---|---|---|---|
| 3,799,743 | 3/1974 | Alexander et al. | 422/68 |
| 3,966,580 | 6/1976 | Janata et al. | 204/403 |
| 4,020,830 | 5/1977 | Johnson et al. | 128/632 |
| 4,072,576 | 2/1978 | Arwin et al. | 435/7 |
| 4,081,334 | 3/1978 | Suzuki et al. | 204/1 T |
| 4,151,049 | 4/1979 | Janata | 204/1 T |
| 4,218,298 | 8/1980 | Shimada et al. | 204/418 |
| 4,321,123 | 3/1982 | Nakamura et al. | 204/403 |
| 4,388,165 | 6/1983 | Koshiishi et al. | 204/418 |

OTHER PUBLICATIONS

FEBS Letters, vol. 109, No. 2, pp. 252–256, Jan. 1980.
Sternberg et al., J. Colloid & Interface Science, vol. 72, No. 2, pp. 255–264, Nov. 1979.
Bergveld et al., Med. & Biol. Eng. & Compt., 17, pp. 647–654 (1979).
Bergveld et al., IEEE Trans. BMI-23, pp. 136–144, (1976).
Zemel, Surface Science, 86, pp. 322–334, (1979).
Lauks et al., IEEE Trans. Electron Devices, vol. ED-26, No. 12, pp. 1959–1964, Dec. 1979.
Bergveld, Composant Biomedical, vol. 57, pp. 451–454, (1977).
Murray, Acc. Chem. Res., 13, pp. 135–141, (1980).
Bergveld et al., Nature, vol. 273, Jun. 8, 1978.
Hafeman et al., Proc. Natl. Acad. Sci. USA, vol. 78, No. 7, pp. 4552–4556, Jul. 1981.
von Tscharner et al., Biophys. Journal, vol. 36, pp. 421–427, Nov. 1981.
Wen et al., IEEE Trans. Electron Devices, vol. ED-26, No. 12, Dec. 1979.

Primary Examiner—G. L. Kaplan
Attorney, Agent, or Firm—Bertram I. Rowland

[57] ABSTRACT

Electroanalytical elements are provided involving a polarity-sensitive layer; a first lipid layer non-diffusively bound to said polarity-sensitive layer; and, a second amphiphilic layer, with hydrophilic heads distal from said first lipid layer and defining a polar layer which interacts with said polarity-sensitive layer. The device is used in polar media to detect variations in the electrostatic interaction between the polar layer and the polarity-sensitive layer.

23 Claims, 6 Drawing Figures

LIPID MEMBRANE ELECTROANALYTICAL ELEMENTS AND METHOD OF ANALYSIS THEREWITH

CROSS-REFERENCE TO RELATED APPLICATIONS

This application is continuation-in-part of application Ser. No. 463,577, filed Feb. 3, 1983 and now abandoned, whose disclosure is incorporated herein by reference.

BACKGROUND OF THE DISCLOSURE

1. Field of the Invention

The ability to measure events, the presence of specific materials, and rates of reaction; the detection of disease states; the increase in sensitivity of measurements, and the like, has undergone enormous elaboration in the variety of techniques, protocols, and materials used. The ability to measure a specific compound, mixture of compounds, aggregation or complex unit in a medium is of interest to such diverse applications as process monitoring, pollutants in air and water, drug determinations in physiological fluids, disease diagnosis, histocompatibility between individuals, food quality and the like. Concentrations of interest may vary from molar to picomolar or less.

Because of the wide diversity of materials of interest, environments in which measurements are to be made, variations in sensitivity, as well as the information desired, numerous reagents, devices and protocols have been developed having varying degrees of specificity, modes of application, sophistication and complexity. Nevertheless, there still remains opportunities for new devices employing novel protocols, which can be used as rapid sensitive detection methods to determine changes in an environment, the presence of a particular substance or group or aggregation of substances, or the like.

There is also an interest in being able to control spatial relationships between diverse compositions. The capability of defining spatial relationships between compositions would be of significant importance in understanding molecular interactions, providing for novel processes and performing specific manipulations at molecular levels.

2. Description of the Prior Art

Representative literature disclosures of such processes and the electroanalytical elements they employ include for example, *FEBS Letters* Vol. 109, No. 2 (January 1980) pages 252–6 entitled "Some Different Ways to use Adsorption of Molecules on Electrodes to Measure Enzymatic Activity" by Arwin and Lundstrom; *Journal of Colloid and Interface Science* Vol. 72, No. 2 (November 1979) pages 255–264 entitled "Silicon-Silicon Dioxide as an Electrode for Electrical and Ellipsometric Measurements of Adsorbed Organic Molecules" by Stenberg, Arwin and Nilsson; *Med. and Biol. Eng. and Compt.*, 1979, 17, 647–654, entitled "From Conventional Membrane Electrodes to Ion-sensitive Field-effect Transistors" by Bergveld and de Rooij; *IEEE Trans* BMI-23, (1976), pages 136–144, entitled "Extracellular Potential Recordings by Means of a Field Effect Transistor Without Gate Metal, Called OSFET" by Bergveld, Wiersma and Meertens; *Surface Science* 86 (1979) pages 322–334 entitled "Chemically Sensitive Devices" by Zemel; *IEEE Transactions on Electron Devices* Vol. ED-26, No. 12, (December 1979), pages 1959–1964, entitled "The $Si_3N_4/Si$ Ion-Sensitive Semiconductor Electrode" by Lauks and Zemel; and *Composant Biomedical* Vol. 57, (1977) pages 451–454 entitled "Ion-Sensitive Field Effect Transistor" by Bergveld.

Patent disclosures concerning this subject include, for example, U.S. Pat. No. 3,966,580 of Janata et al.; U.S. Pat. No. 3,799,743 of Alexander et al.; U.S. Pat. No. 4,072,576 of Arwin et al.; U.S. Pat. No. 4,020,830 of Johnson; and U.S. Pat. No. 4,321,123 of Nakamura et al.

SUMMARY OF THE INVENTION

An electroanalytical device and methods for its use are provided, where the device employs a solid electrically-sensitive layer which allows for the determination of an electrical property, a first lipid layer non-diffusively bound to said electrically-sensitive layer, a two-dimensional amphiphilic layer having hydrophobic chains proximal to said first lipid layer and polar heads distal from said first lipid layer and defining a polar layer. The polar layer electrostatically interacts with the electrically-sensitive layer. By introducing the device into a polar medium, variations in the effect of the polar layer on the solid electrically-sensitive layer as determined by variations in an electrical signal can be related to specific events.

BRIEF DESCRIPTION OF THE DRAWINGS

The invention will be described with reference being made to the accompanying drawings in which.

DESCRIPTION OF THE SPECIFIC EMBODIMENTS

Figure 1:
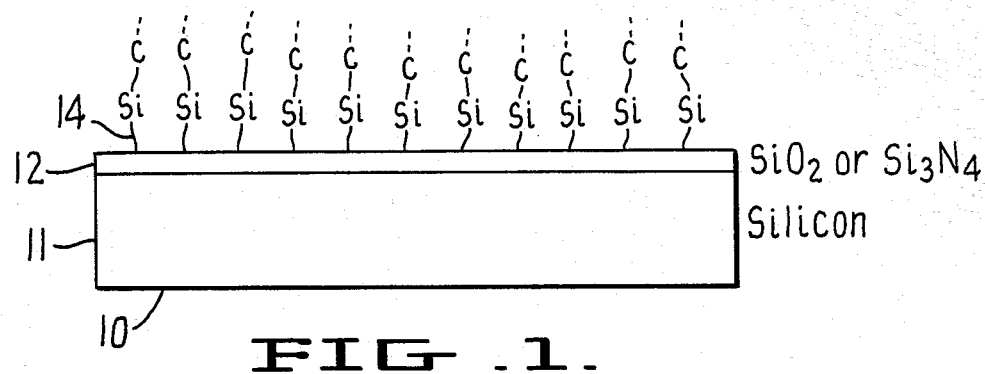
FIG. 1 is an expanded scale cross-section of a typical hydrophobically primed electroanalytical surface.

The subject invention involves a novel device having a first solid layer which is conductive or semiconductive and is able to sense changes in polarity, e.g., charge. The solid conducting layer is separated from a charged layer by a lipid bilayer. The lipid bilayer is composed of a first lipid layer which is non-diffusibly bound to said solid layer and a second lipid layer which may be capable at least in part of lateral diffusion and physically adjacent to but not covalently bound to the first lipid layer. Attached to the distal ends of the second lipid layer are polar hydrophilic heads which may be charged or uncharged, and define a polar layer. The polar layer provides for a dipolar or an electrostatic layer which may be sensed by the solid conducting layer, as well as allowing for various chemical or physical interactions to occur at this layer.

The device is employed in a polar, normally aqueous, medium where events which vary the observed electrical signal as a result of the interaction between the polar layer and solid conducting layer are detected and can be related to the specific event.

In describing the invention, a number of terms will be used which for purposes of clarity will be defined:

An "electroanalytical element" is a solid metallic or non-metallic (semiconductive) electrode or transistor device, which acts as polarizable charge-sensing element. These elements include conducting metallic electrodes, electrodes made of semiconducting material, such as silicon, germanium, gallium arsenides, indium arsenides, and the like, as well as such semiconducting materials in transistor device configurations capable of sensing the presence of charge and/or electrically polarized substances.

An "amphiphilic molecule" is a molecule which includes a hydrophobic region, namely a lipid region, and a hydrophilic head or terminus, which is polar, may be charged, uncharged, may have a residual charge or be electrostatically neutral. Ionic groups include ammonium, phosphonium, sulfonium, etc., for positive charges; while for negative charges, groups will include carboxylate, sulfonate, phenoxide, sulfate, phosphate, borate, etc. Groups which are neutral, but are polar, include nitroxy, azoxy, betaines, nitro, hydroxy, etc. Neutral polar groups include ethers, esters, amides, carbonyls, etc. Desirably, the polar group will be charged having a residual charge or be neutral. Included in the definition of "amphiphilic molecules" are "bilayer-formable amphiphilic molecules", which molecules form a stable bilayer lamellar phase in polar media, particularly aqueous media.

In describing the subject invention, the structure of the device will be considered first, followed by various methods in which it may be used. After consideration of the drawings, applications of the device and methods will be exemplified.

The solid electrically-sensitive layer may be composed of metals or non-metallic semiconductive materials, which will be responsive to electrostatic charges resulting from charged atoms or dipoles. The solid layer will usually have a non-conductive surface which permits binding or bonding of the first lipid layer to the surface, to form a non-diffusible lipid layer.

The solid electrically conducting layer may be a simple metallic strip, wire or other configuration or may include a wide variety of devices, which allow for detection of changes in polarity to be detectable in an external circuit. The change in electrical signal can be as a result of a change in impedance, capacitance, conductance, or inductance.

Metallic devices may include metal electrodes, such as silver, gold, palladium, nickel chrome, platinum, etc., where the surface is modified, such as by the formation of oxides, to provide for chemically reactive sites, or complexation is employed. Preferably, and of greater interest are semiconductors, which will be employed in various constructions and materials. Semiconductors may be prepared from silicon, gallium, gallium arsenide, aluminum gallium arsenide, etc., where the material may be doped with various donor or acceptor atoms, e.g., boron, aluminum, nitrogen, arsenic, antimony, phosphorus, or the like.

By varying the organization of the solid conductive layer, the response to the external environment and the manner of measurement may be varied. Constructions may include devices such as FET, MOSFET, AEFET, OSFET, ISFET, etc. The particular construction is not critical to the subject invention, so long as an electrical signal can be developed by varying the interaction between the solid conductive layer and the polar layer.

The surface of the solid conductive layer may be an inert non-conductive layer, particularly for non-metallic conductive layers, which inert layer is capable of forming strong bonds, either directly or indirectly, to lipid molecules. Therefore, for the most part, the surface will be a metal or non-metal oxide or nitride which is capable of reacting with a non-metal halide or oxide to form a strong covalent bond. For metallic layers, either bonding or complexation may be employed. The bonding can be through conventional chemical means such as oxidation or nitridation with heat and oxygen or nitrogen, exposure to strong oxidizing acids such as $HCl/HNO_3$, or through electrochemical electrode oxidation processes. Complexation with metals or metal compounds can be achieved with chelating agents, such as alkyl nitrides, EDTA, EGTA, NTA, etc. Murray, *Acc. Chem. Res.* (1980) 13:135–141, describes techniques for coupling organic species to metal electrode surfaces, which disclosure is incorporated herein by reference.

The non-conductive chemically reactive layer will be at least about 10Å and usually not more than about 1500Å (0.15$\mu$), depending upon the function(s) of the layer. For example in gate regions of oxide FETs, layers of about 0.1–0.15$\mu$ may be formed, employing, for example, thermal process (Gosling et al., Field Effect Electronics, Chapter 3, Butterworth, London, 1971, incorporated herein by reference). However, in the subject invention, the layer will usually be relatively thin, ranging from about 10Å to 0.1$\mu$, usually 10Å to 500Å, more usually 10Å to 100Å.

The solid conducting layer may be constructed in a variety of ways to allow for detection of change in polarity, by being able to measure a change in impedance, capacitance, conductance, or inductance. Thus, with semiconductors, various transistor devices may be developed where one or a plurality of sites may be doped with donor or acceptor atoms and one or a plurality of other sites may be doped with complementary donor or acceptor atoms to provide for a single or plurality of regions where an electrical signal may be detected as a result of change in polarity using varying external circuits to monitor the change.

By having one or a plurality of regions isolated from each other and adjacent to the insulating layer of a solid conductor, the electrical properties of these regions may be modulated by variations in the polarity, including charges, adjacent to the surface. For example, with a field effect transistor, the electrical nature of the gate region can be modified by varying the charge in the region of the polar layer defined by the amphiphilic layer. The charges may be varied either between the solid conductive layer and the polar layer or at or adjacent to the polar layer. The variation can be determined by a change in current, resistance or voltage. In a bipolar transistor, by modifying the electrical properties of an isolated region adjacent the surface, which region is connected to an external circuit, one can modulate the amount of current which flows through the transistor. Thus, in each situation, the semiconductor device will be sensitive to changes in the polar environment at or adjacent to the two lipid layers.

The first lipid layer will be prepared from lipids having a reactive terminus, which can covalently react with the oxide layer on the solid conductive layer or complex with the oxide or metal layer. This lipid layer may be prepared from a single compound or a plurality of compounds, generally having an aliphatic chain of at least about 6 carbon atoms and not more than about 30 carbon atoms, preferably from about 8–20 carbon atoms. The carbon atoms may be bonded to hydrogen or other non-polar heteroatoms which provide for an inert hydrophobic compound. Particularly, halocarbons, more particularly fluorocarbons, may be employed.

For the most part, silylation will be employed for binding to the solid surface, where a silyl halide, particularly silyl mono-, di- or trihalides may be employed. The silylation can be effected by contacting a clean oxide or nitride surface with a molar excess of the organo-silane reagent(s) and then curing. Alternatively, siloxanes may be employed with oxide layers.

The silylation reagents employed are most commonly alkylsilane halides or oxides and derivatized alkylsilane halides or oxides. These materials have the formula

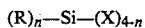

wherein:
n is an integer 1, 2 or 3;
R is, in each of the n units, independently selected from alkyls and derivatized alkyls, of up to about 30 carbon atoms, at least one R having a chain of six carbon atoms; and
X is a halo, such as Cl, or alkoxide of from one to three carbon atoms.

Such reagents include monoalkyl trihalosilanes, dialkyl dihalosilanes, trialkyl monohalosilanes, monoalkyl trialkoxysilanes, dialkyl dialkoxysilanes and trialkyl monoalkoxysilanes, as well as such silanes whose alkyl groups have been derivatized so as to include amines, acyl groups, aryls, alkaryls, thiocyanate groups and the like. The alkyls can contain minor amounts of olefinic unsaturation and minor degrees of branching, i.e., methyl branches, and the like to lower their melting point. A range of silylation reagents are available commercially from Petrarch Systems, Inc., Bristol, Pennsylvania.

Representative silylation reagents include dihexyldichlorosilane, heptyltrichlorosilane, heptylmethyldichlorosilane, dodecyltrichlorosilane, methylhexadecyldichlorosilane, octadecyltrichlorosilane, dimethyloctadecylchlorosilane, eicosyltrichlorosilane, eicos-8-enyltrichlorosilane, 1-methyleicosyltrichlorosilane; their bromo analogs; and the like. Other materials can be provided by processes of the art, if desired. Preferred silylation reagents are the $C_6$ to $C_{30}$ and more preferably, $C_{14}$ to $C_{24}$, mono-, di-, and trialkyl silane halides, with the monoalkylsilanes being most preferred. Mixtures of two or more lipid agents may be employed.

The text *Silane Coupling Agents* by Plueddemann (Plenum Press, New York) discloses other silylation agents and is incorporated herein by reference.

The first hydrophobic layer is a relatively rigid layer, which is non-diffusible, and to the extent the same or similar aliphatic chains are employed, will provide an oriented structure. In contrast to this is the second lipid layer, which is not covalently bound, but rather has molecules which may or may not be diffusible, preferably being diffusible at least in part, in two dimensions and is bound to the first lipid layer by hydrophobic interactions. Thus, the second lipid layer may respond to changes in its environment with movement of individual molecules in response to such changes. In addition, the second lipid layer can accommodate various molecules internal to the layer or extending through the layer.

The second lipid or hydrophobic layer will be made of molecules capable of forming a bilayer. The amphiphilic materials include alkylene oxide polymers, particularly ethylene and/or propylene homo- or copolymers or molecules having aliphatic chains of at least about 6 carbon atoms and not more than about 30 carbon atoms, where the amphiphilic compound may be alkyl, alkaryl or alkyl-substituted carbocyclic compounds. Particularly, various steroids may be employed in combination with the other hydrophobic molecules of the layer.

Lipids which may be used in the present invention include any bilayer-formable natural or synthesized polar lipid. The term "lipid" is used broadly to include the saponifiable lipids, such as acylglycerols, phosphoglycerides, the sphingolipids, gangliosides and waxes and the like. The lipid layer may also contain simple lipids, such as terpenes and steroids, so long as its overall character is "bilayerformable." Chapter 11 of the text *Biochemistry* (Second Edition) by Lehninger, (Worth Publishers, Inc., New York) which is incorporated herein by reference, shows a wide range of possible lipid materials.

Without intent to exclude other equivalent materials, the phospholipids are generally preferred. These materials can carry charges or be uncharged. Typical lipids employed herein include phosphoglycerides having phosphatidylethanolamine, phosphatidylcholine, phosphatidylserine, phosphatidylinositol, phosphatidylglycerol, and cardiolipin head groups. Some specific nonlimiting examples of useful lipids include: dipalmitoylphosphatidylcholine, distearoylphosphatidylcholine, dimyristoylphosphatidylcholine, dimyristoylphosphatidylethanolamine, and the like. Mixtures of these materials may be used.

The diffusible fluid monolayer can be applied to the support surface by drawing the support surface through a previously-formed fluid monolayer floating on a liquid surface, such as with the Langmuir method, Langmuir and Schaefer *J. Am. Chem. Soc.* (1938) 60:383–398. The use of this method to form lipid monolayers on support surfaces on glass is demonstrated by von Tscharner and McConnell *Biophys. J.*, Vol. 36, pages 409–419, incorporated herein by reference. See also, Montal and Mueller, *Proc. Natl. Acad. Sci. USA* (1972) 69:3561 and Benz et al., *Biochem. Biophys. Acta* (1975) 395:323.

Very briefly, the monolayer can be formed by being spread as a nonaqueous solution on a fluid surface (usually water). The nonaqueous solvent is evaporated and the monolayer is compressed horizontally on the fluid surface to a desired packing density, allowed "to equilibrate", and then applied to the support layer on the element. It is preferred that the degree of compression should be great enough to assure a continuous fluid membrane. Such membranes are characterized by having surface pressures of at least 10 dyne/cm.

The casting solution is made up in any solvent to which the amphiphilic materia is inert and which will reasonably rapidly evaporate when the membrane is cast.

Alternatively, one may use a partially or completely cross-linked hydrophobic layer, by employing unsaturated, particularly polyunsaturated lipids. The unsaturated lipids may be cross-linked, in whole or in part, by employing various polymerizing catalysts, e.g., free-radicals, high energy radiation, etc., or other cross-linking agents, to provide a relatively rigid layer, with the lipid chains in substantially parallel vertical orientation. See, for example, Gros, Ringsdorf & Schnepp, Angewandte Chemie (1981) 20:305–325, which disclosure is incorporated herein by reference. Depending on the degree of cross-linking, the presence of saturated or mono-olefinic lipids, and the like, the layer will have more or less capability for lateral diffusion.

For preparing the bilayer membrane, the second layer need only be laid down upon the first layer to provide for stable hydrophobic interaction. This greatly simplifies preparation of the bilayer membrane and allows for the chemistry to be carried out on the second layer to provide for desired modifications.

The second hydrophobic layer defines a polar layer at its surface distant from the first hydrophobic layer. The polar layer plays a plurality of roles. First, it is necessary for the formation of the monolayer and for the retention of the integrity of the monolayer. Secondly, it provides a polar, usually electrostatically charged, layer which affects the properties of the solid conductive layer. Third, the polar molecules can be modified in a variety of ways, so as to be bound covalently or non-covalently to a wide variety of molecules for diverse purposes. Fourthly, the environment about the polar molecules may be modified in a variety of ways so as to change the nature of the interaction between the polar layer and the solid electrically conductive layer to provide a change in electrical signal which can be related to the change in environment of the polar layer. Finally, the second hydrophobic layer can accommodate a variety of molecules having polar and non-polar domains, where the non-polar domain may be stably retained in the hydrophobic region of the second layer, or hydrophobic ions.

The polar heads may be modified by including various complexing agents, particularly complexing agents which are specific for a particular ion or molecule. Crown ethers, cryptates, EDTA, NTA, porphyrins, or other neutral or charged species may be employed.

A second group of substances which may be used to modify the second layer lipids involves organic molecules which have a specific affinity for each other and are referred to as specific binding members, i.e., ligands and receptors. The ligands are normally classified as haptens and antigens, depending upon their immunologic response and receptors can be a diverse group of materials, which includes naturally occurring receptors, such as surface membranes, enzymes, antibodies, lectins, or the like.

Representative couplings of halves of immunochemical pairs to lipids is shown in Brulet and McConnell, *Biochemistry* (1977) 16:1209–1217 and in Hafeman, von Tscharner and McConnell, *Proc. Natl. Acad. Sci. USA* (1981) 78:4552–4556, which are incorporated herein by reference. As these articles show, a lipid having an immunologically active material bound to it can be included in a fluid monolayer; and the immunologically active material maintains its activity when so bound. One can use the subject device in a wide variety of ways by employing varying combinations of ligands, receptors and, as appropriate, labels which provide for a particular manner for modulating the electrical signal from the solid electrically conductive layer.

Of particular interest for labels are catalysts, particularly enzymes, charged molecules, metal particles, e.g., magnetic or magnetizable particles, or the like.

A variety of small molecules or large molecules can be covalently or non-covalently bound to the members of the second hydrophobic layer. Where one wishes to determine the presence of an analog of such molecules in a sample, one can provide for competition between the molecules in the sample and the molecules bound to the second hydrophobic layer. By labeling receptors, the number of receptors capable of binding to the second hydrophobic layer will be proportional to the amount of analyte in the sample.

Particularly, one could use a catalyst, preferably an enzyme, as a label. By employing a substrate which results in the production of charged molecules, where the number of enzyme molecules bound to the second hydrophobic layer is related to the amount of analyte in a sample, one can relate the observed signal to the amount of analyte in the sample.

Alternatively, one could employ coenzymes and use an apoenzyme as a label, where antibody binding to the analyte bound to the coenzyme would inhibit its binding to the apoenzyme. Therefore, the amount of enzyme which would bind to the coenzyme would be related to the amount of analyte in the sample. Again, the observed electrical signal could be related to the amount of analyte in the sample.

The subject device can also be used for the sensitive detection of large aggregates, such as are present with microorganisms as illustrated by viroids, viruses, bacteria, fungi, algae, and the like. By employing antibodies which bind to a specific surface feature, such as a protein or polysaccharide, the microorganism would bind to a plurality of the receptors bound to the second hydrophobic layer. By employing different receptors, which are specific for a particular strain, and optionally by varying the conditions of the medium so as to change binding affinities, and observing the change in binding of the microorganism to the second hydrophobic layer, one could detect not only the presence of a particular species, but also a particular strain. Since the organism would be large, its presence would substantially affect the nature of the polar layer, so as to provide a change in signal in the solid conductive layer.

In addition, the subject device would be sensitive to changes in pH, ionic strength of the medium, or other bulk change in the medium which would affect the electrostatic influence of the polar layer on the solid conductive layer.

In another aspect, hydrophobic ion compounds may be employed, which are ionic or non-ionic and which will preferentially insert themselves in the lipid layer and can affect the electrostatic field imposed upon the solid conductive layer. The hydrophobic compound may be a hydrophobic ion, such as tetraphenylboron or dipicrylamine which are anions, or tetraphenylphosphonium ion which is a cation. Other molecules which may be employed include peptide or peptide-like substances, which bind to membranes and facilitate the passage of ions. Illustrative of these materials are melittin, alamethicin, valinomycin and the polyene antibiotics. These materials may be used by themselves or coupled to other compounds, such as ligands or receptors, whereby the binding of a ligand or receptor to its homologous binding member can be detected by the amount of the available hydrophobic molecule which is present in the lipid bilayer.

Illustrative of such an assay would be a hapten bound to a hydrophobic compound, where antibody is bound to a solid support. By having a competition between the conjugated hapten and the hapten in a sample for the antibody bound to the solid support, the concentration of the hydrophobic conjugate in the medium and available for insertion into the hydrophobic layers would be related to the amount of hapten or analyte in the sample.

A further exemplification of the use of the subject device is the measure of capacitance based on the ability of a lipid layer to solidify or crystallize. The phase transition between solid and fluid can be detected electrically by the change in capacitance.

In another illustration, one could employ materials which are capable of lysing the lipid layer or breaking down its integrity. Illustrative of such a material is complement or various components or combinations of components which are included under the term complement. When complement binds to an antibody which is bound to the lipid layer, one can relate the disorder of the lipid layer by employing a combination of antibody and complement, where the homologous ligand is bound to the second lipid layer. Enzymes can also be used for breaking down the lipid layer, for example, lipases, phosphatases, esterases, or proteases, where the polar head is sensitive to hydrolysis by the ester. Various techniques can be employed, where the available amount of active enzyme can be related to an analyte of interest. See, for example, U.S. Pat. No. 3,817,837.

Figure 2:
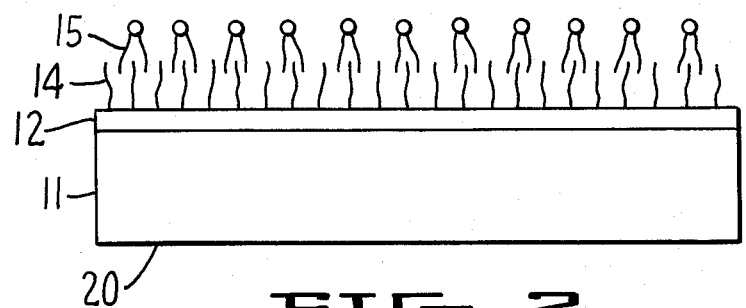
FIG. 2 illustrates the surface of FIG. 1 with the added fluid monolayer.

For further understanding of the subject invention, the drawings will now be considered. FIGS. 1 and 2 illustrate a conducting or semiconducting body, having an insulating coat and a lipid layer. In FIG. 1, an electroanalytical element 10 is shown including body 11, which is indicated as a semiconductor and is composed of silicon and an insulating layer 12, which is silicon dioxide or silicon nitride. The insulating layer 12 is chemically reactive and an organic hydrophobic layer 14 is bound to the insulating layer 12 by means of silicon bonds. In FIG. 2, the components of FIG. 1 are designated as 20 and an additional bilayer-formable layer of amphiphilic molecules is indicated as 15.

Figure 3:
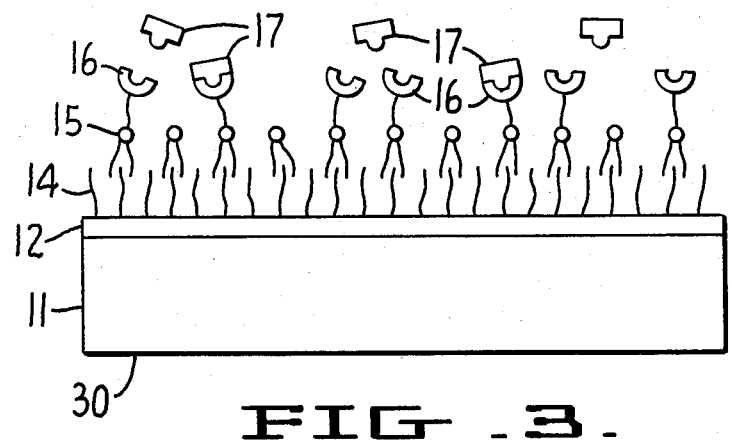
FIG. 3 illustrates the surface of FIG. 1 with an added fluid monolayer that is immunologically active.

In FIG. 3, the use of the device in combination with specific binding pair members is indicated. In FIG. 3, the components of FIG. 1 are referred to as element 30 with second hydrophobic monolayer 15. Molecules of the second monolayer are joined to a receptor 16 of a ligand-receptor pair, for example, an antibody. The homologous hapten or antigen 17 in solution binds to the receptor 16 changing the electrostatic field in the polar layer which can be detected by the element 30.

Figure 4:
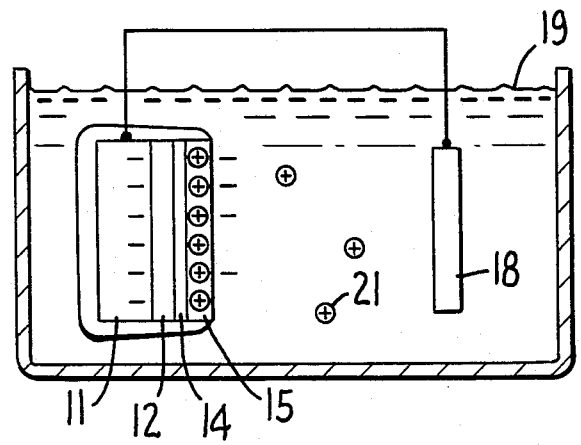
FIG. 4 shows a schematic view of the electrical charge distribution when an electrode of the invention detects a charged species.

FIG. 4 illustrates the situation with the device of the subject invention and the use of hydrophobic ions. A liquid sample 19 contains hydrophobic cations 21, which become inserted into the hydrophobic layer 15. A countercharge (Gouy-Chapman) double layer is created at the hydrophobic layer-sample interface. When, as in FIG. 4, a reference electrode 18 is present to complete the circuit, an additional countercharged layer appears in the electrode body 11. This charge on the electrode can be measured and related to the presence or absence of charge species 21 in the test sample.

If the hydrophobic layer 15 incorporated one-half of a ligand-receptor binding pair, while the homologous binding member was conjugated to a hydrophobic ion, binding of such conjugate to the hydrophobic layer 15, would buildup an electrostatic field in the region of the polar heads of the hydrophobic layer 15.

Figure 5:
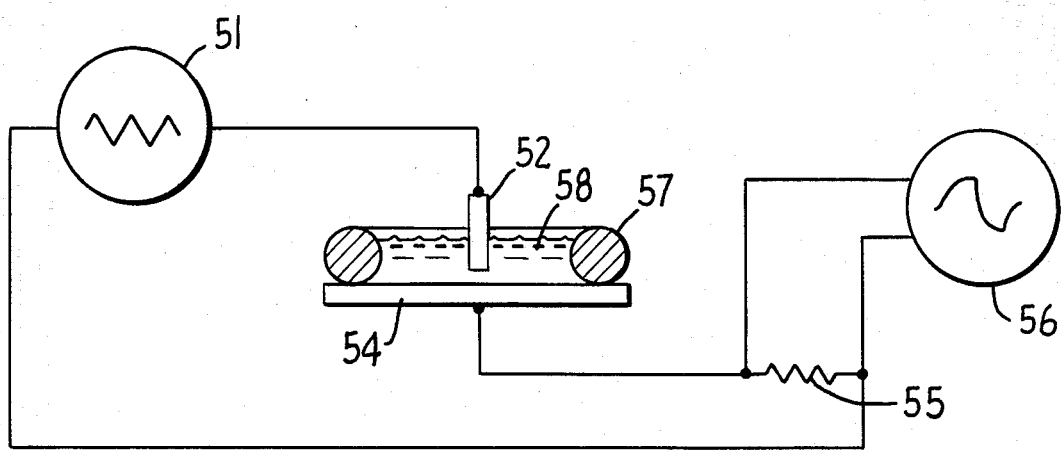
FIG. 5 shows a schematic view of an analytical device employing an element of the invention as an electrode to measure capacitance.

In FIG. 5, a simple circuit for measuring capacitance changes is illustrated, where the device of the subject invention is employed. A signal source 51 is illustrated, which provides a signal, such as a triangular pattern of known voltage amplitude. A reference electrode 52 is connected to the source 51. An electroanalytical element of the subject invention 54, a resistor 55 and an oscilloscope 56, which measures the saturation voltage reached as a signal oscillates, completes the circuit. Electrode 54 is a 1.75 cm$^2$ area disk of silicon with an ohmic electrical contact affixed to its back side. Electrode 54 provides a bottom surface of a 2 cc sample zone defined by O-ring 57. Aqueous sample 58 is in contact with the reference electrode 52 which is spaced about 5 mm from electrode 54. Capacitance is calculated by the formula $C=V/RK$, where V is the measured saturation voltage, R is a known resistance and K is a gradient obtained from the point-to-point voltage in the oscillator frequency.

Capacitance measurements are sensitive to the presence of hydrophobic electroactive species in the second hydrophobic layer and to the integrity and physical state of the second hydrophobic layer. Thus, various changes in the second hydrophobic layer can be detected.

For example, the capacitance of element 54 having a dimyristoylphosphatidylcholine hydrophobic layer is determined to be 1.02 microfarads at a temperature below the solid-liquid phase transition. When the temperature was raised to above the phase transition, the capacitance immediately rose to 1.20 microfarads. This sharp change at the phase transition temperature occurs only if an intact monolayer is present and can be used to indicate the integrity of the monolayer if desired.

The electronics of this relatively simple measurement system provide but one example of circuitry. One could achieve greater sensitivity in a number of ways—for example, one could read the saturation voltage over a period of time and average the values; one could use a precision high impedance voltmeter, as is shown in Lauks and Zemel *IEEE Trans. on Electric Devices,* Vol. ED 26, No. 12, December 1979, or one could use an impedance bridge to measure capacitance as is known in the art.

Using any of these methods one could employ the electrode of the invention to detect half of a ligand-binder pair. For example, one could hydrophobically prime the silicon wafer with an eighteen carbon thick support layer and apply thereover a fluid monolayer of a hapten-bound lipid. A typical haptenbound lipid is dipalmitoyl phospholipid nitroxide hapten described and prepared as shown in the article by Hafeman, von Tscharner and McConnell, *Proc. Natl. Acad. Sci. USA* (1981) 78:4552–4556.

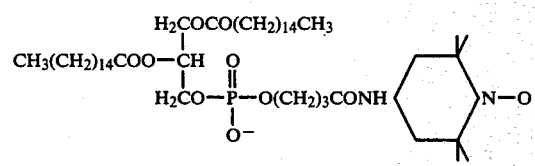

The hapten-bound element is employable in a measurement of the presence of anti-nitroxide IgG antibody (prepared in rabbits by the method of Humphries and McConnell, *Biophys. J.,* (1976) 16:275–277) in aqueous buffer solution. The electrode configuration of FIG. 5 is used. The hapten-bound element and a platinum wire reference electrode are placed in contact with the buffer solution and the capacitance between them is measured by means of an impedance bridge, a signal generator and an amplifier with a zero detector. The capacitance between the electrodes is determined by the degree of electrode polarization and the extent to which species are adsorbed onto the electrodes. When the anti-nitroxide IgG antibody is added to the solution it is selectively bound to its cognate in the fluid monolayer surface and the capacitance measured by the bridge changes. When this measurement is repeated adding an equimolar amount of an organic material that does not form an immunochemical pair with the electrode surface, no change in capacitance is observed.

Figure 6:
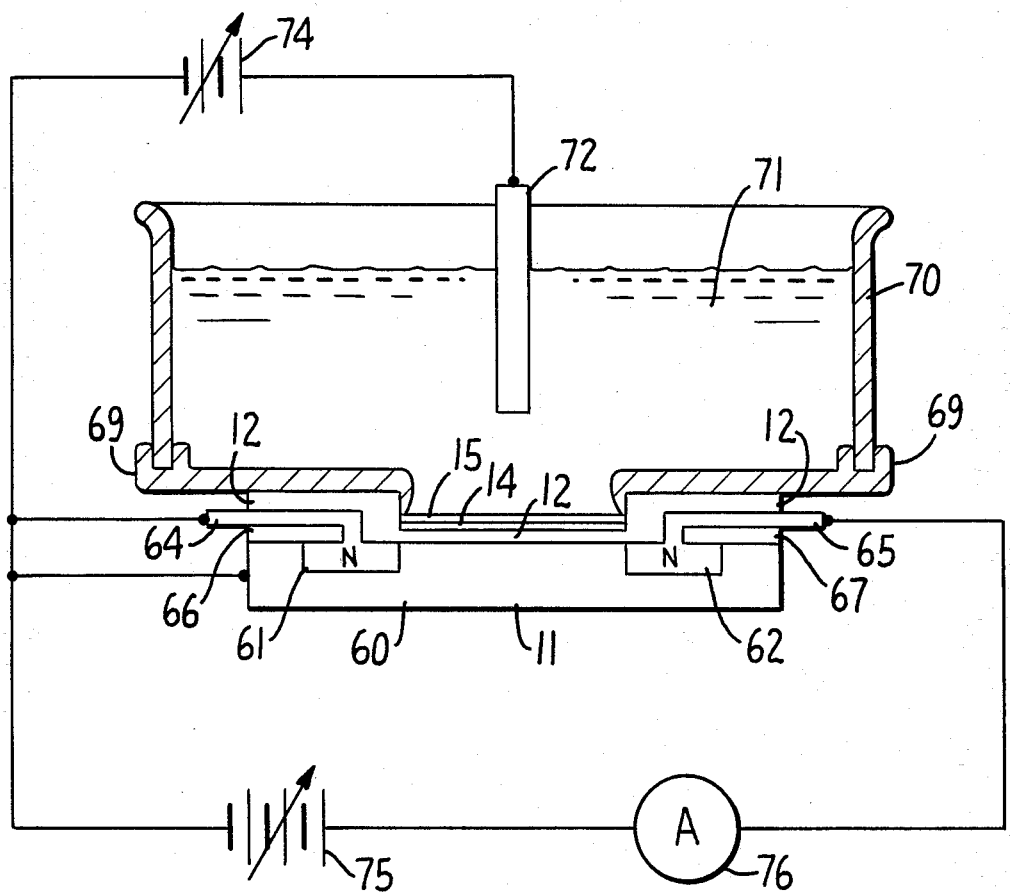
FIG. 6 shows a schematic cross-sectional view of a field effect transistor employing an element of this invention as its gate region.
Figure 1:
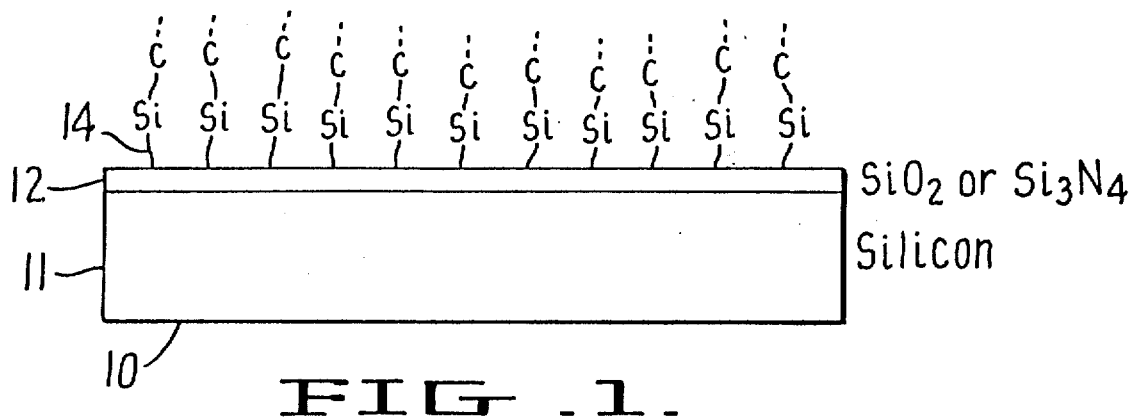
Figure 2:
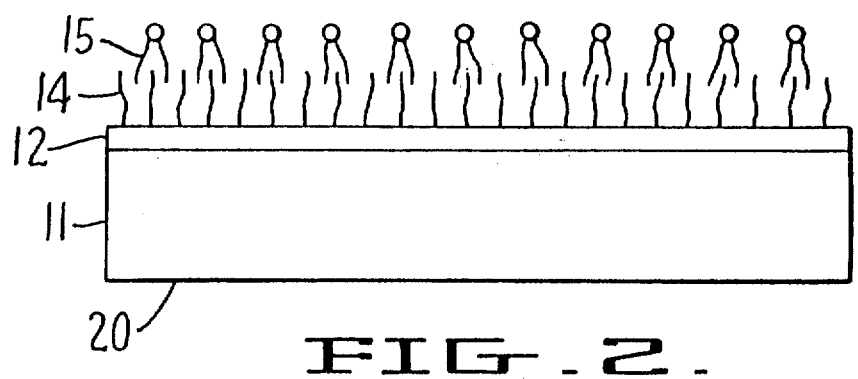
Figure 3:
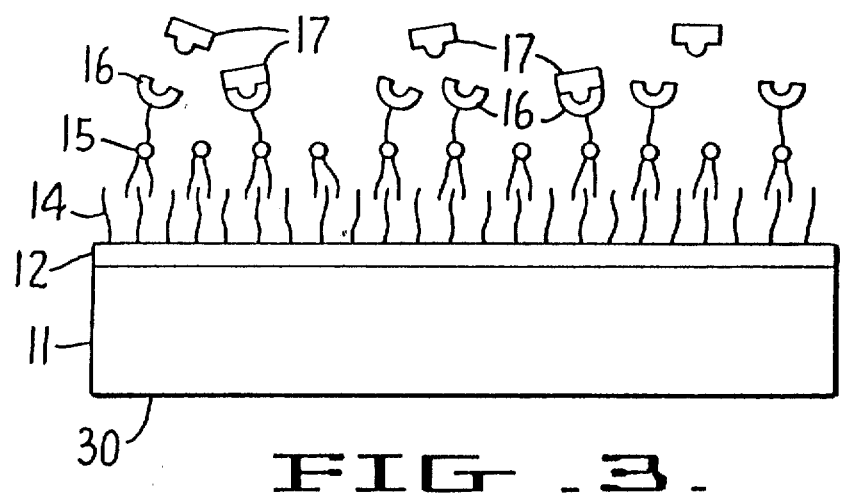
Figure 4:
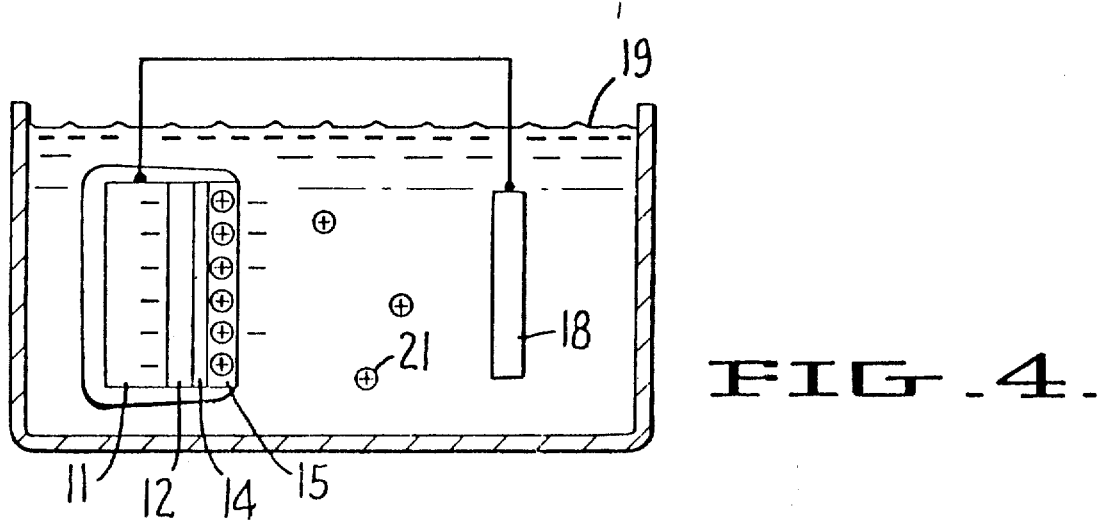

In FIG. 6, an alternative embodiment of the subject invention is depicted, employing a FET. A transducer 60, composed of P silicon body 11 and oxide coating 12 is shown. Transducer 60 is a representative high impedance semiconductor device. Oxide layer 12 is very thin—e.g., 20Å in the center area. Transducer 60 additionally includes N source region 61 and N drain region 62. These regions communicate with conductor layer 64 and 65 and are insulated from body 11 by insulator regions 66 and 67. A water-impermeable covering 69 protects oxide layer 12 and couples to sample vessel 70. The portion of transducer 60 which communicates with sample vessel 70 has been primed with trichlorooctadecylsilane to form a monolayer support surface 14, and then treated to add a fluid lipid monolayer 15. The region of transducer 60 where the support layer and lipid layer are present is the gate region in a field effect transistor configuration. In this configuration transducer 60 can serve as a very sensitive detector.

A solution 71 with which the gate region of transducer 60 is contacted is placed in vessel 70. A reference electrode 72, such as a platinum wire electrode, is placed in contact with solution 71 as well to establish a reference voltage for operation of transducer 60. The reference electrode 72 is coupled to a voltage source 74 which develops the desired reference voltage. A voltage source 75 is also provided between the source electrode 64 and drain electrode 65 to establish a potential difference sufficient to cause current flow in the conducting channel between diffusion regions 61 and 62. An ammeter 76 is coupled in series between the voltage source 75 and the drain electrode 65 for measuring the drain current.

When transducer 60 is exposed to a solution 71 containing hydrophobic ions which will specifically interact with fluid lipid monolayer 15, the transducer operates in a fashion similar to that shown with FIG. 4. That is, when the reference electrode 72 is properly biased, ions in the solution 71 create a potential difference between the monolayer and the solution. This creates an electric field in the conducting channel. The strength of this field, which is dependent upon the concentration of ions in the solution, controls the magnitude of current flow through the conducting channel and thus the magnitude of the drain current. The drain current is measured by the ammeter 76 which thus provides a measure of the ion concentration in the solution.

The various devices can be miniaturized and, furthermore, a plurality of devices can be located on a single silicon semiconductor chip, thus, a plurality of electrodes, transducers, FET devices, or the like can be fabricated in a single chip. Thus, a single chip can provide for a plurality of determinations of the same or different substances.

To prepare an appropriate device, the following procedure may be employed.

When the hydrophobic priming involves silylation, it is generally advisable to exclude water and to have a scrupulously clean element surface. In the case of semiconductor surfaces, it is sometimes desirable to pretreat the surfaces with aqueous hydrofluoric acid prior to drying. Typically, the element surface is cleaned such as by washing with alcohols, ketones, halocarbons, halohydrocarbons and the like; dried (often at elevated temperature, e.g., 50° to 150° C.) and then contacted with a solution of the silylating reagents in an aprotic solvent or aprotic solvent mixture. A typical silylation bath contains from about 0.01% to about 1% of silylation reagent(s) in a dry solvent system which might include hydrocarbons including alkanes, cycloalkanes and aromatics, halocarbons and halohydrocarbons such as chloroform, carbon tetrachloride, trichloroethylene; ethers and alkanols and ketones of up to about 6 carbons, and the like. Very often the exact solvent system employed will be dictated in part by the solubility properties of the silylating reagent, which properties are shown in the literature.

It is essential that enough silylating reagent be present to assure that substantially all possible reaction sites react. If the solid conductive layer elements are completely immersed in an equivolume amount of the solution and if the mixture is gently agitated, complete reaction is assured. The reaction period in the bath is usually about 30 min. but times from about 5 min. to 2 hr. can be employed. In general, the times employed should be selected to assure complete reaction which will depend on the temperature employed. The reaction temperature is from about 10° C. to about 75° C., preferably 20°–45° C. As a guide, 20°–25° C. for 30 min. gives full reaction.

Following immersion in the silylation bath, the body is rinsed with a low-boiling aprotic solvent to remove any high-boiling components of the silylation coupling solvent and to remove excess unreacted silylation agent. Then the silane layer is dry-cured at an elevated temperature, such as 50°–200° C. for from about 10 min. to about 6 hr., preferably from 75° C.–175° C. for from about 20 min. to about 4 hr. Similar silylation methods are shown in von Tscharner and McConnell, *Biophys. J.* (1981) 36:421–427 and Weis et al., *J. Biol. Chem.* (1982) 257:6440–6445.

The second lipid monolayer can be formed by being spread as a non-aqueous solution on an immiscible fluid surface (usually water). The non-aqueous solvent is evaporated and the monolayers compressed horizontally on the fluid surface to a predetermined packing density, and allowed to equilibrate. Various materials may be added which are compatible with the monolayer, such as proteins, hydrophobic compounds, or the like. The degree of compression which is employed is at least about 10 dyne/cm. The device may be introduced into the aqueous system and drawn through the monolayer, so that the second hydrophobic monolayer becomes non-covalently bound to the first hydrophobic monolayer to define a bilayer membrane.

A lipid monolayer is formed of distearyl phosphatidyl ethanolamine, distearyl phosphatidyl choline and the amide of phosphatidyl ethanolamine and the O-carboxymethyl derivative of morphine (49.5:49.5:1). The silanized FET device described previously in relation to FIG. 5 is passed through the monolayer to form a bilayer membrane with the morphine in the aqueous phase. The capacitance of the device is determined. Morphine antibodies are added to the aqueous layer and the capacitance determined, which is different from the original value. When immunoglobulin is added to the aqueous layer, there is only a minor change in capacitance.

In accordance with the subject invention, novel devices and methods are provided for detecting variations in a medium capable of maintaining a lamellar lipid layer. The devices can be varied so as to detect ions, ligands, receptors, or other compounds which will affect the polar field resulting from a polar layer insulated from a solid conducting layer by a stable lipid barrier. The devices can be fabricated to have one or more devices on a single chip, so that a plurality of determinations can be made simultaneously or sequentially.

Although the foregoing invention has been described in some detail by way of illustration and example for purposes of clarity of understanding, it will be obvious that certain changes and modifications may be practiced within the scope of the appended claims.

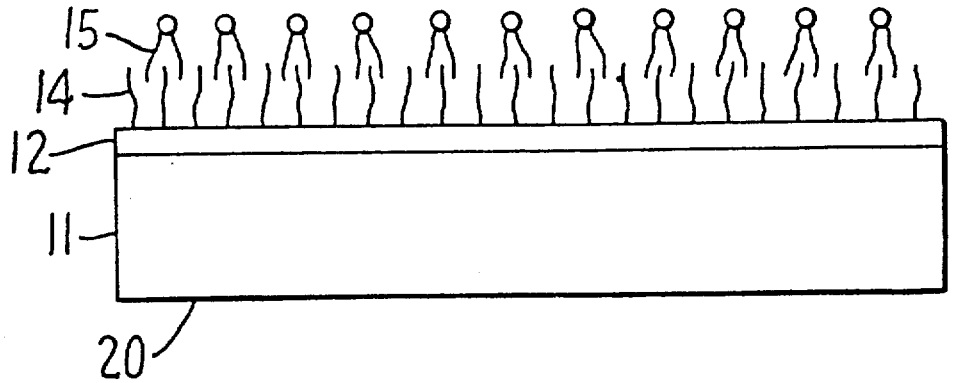

What is claimed is:

1. A device sensitive to changes in polarity, comprising:
    a solid electrically conductive layer having a first surface for binding by chemical means and responsive to changes in polarity adjacent to said first surface;
    a first hydrophobic layer comprising a plurality of molecules having aliphatic chains of at least six carbon atoms, non-diffusively bound to said binding surface;
    a second stable lamellar hydrophobic lipid layer comprising molecules having second chains of at least six carbon atoms and polar heads, with said polar heads defining a polar layer distant from said first hydrophobic layer and separated from said first hydrophobic layer by said second chains of at least six carbon atoms layer, and wherein said individual molecules are laterally diffusible and non-covalently bound to said first lipid layer;
    wherein said first and second hydrophobic layers define a bilayer membrane.

2. A device according to claim 1, wherein said electrically conductive layer is a doped silicon layer, said first surface is silicon oxide, and said molecules of said second layer are individual molecules.

3. A device according to claim 1, wherein said electrically conductive layer is a doped silicon layer, said first surface is silicon oxide, and said molecules of said second layer are at least in part cross-linked.

4. A device according to claim 1, wherein said electrically conductive layer is a doped silicon layer defining an FET device having a gate, with said first surface being silicon dioxide over said gate.

5. A device according to claim 1, wherein said electrically conductive layer is a metal.

6. A device according to claim 1, wherein a specific binding member is bound to said second hydrophobic layer.

7. A device according to claim 6, wherein an enzyme is bound to said second hydrophobic layer.

8. A method for detecting a change in the polarity of a polar medium which comprises contacting a device according to claim 1 with said polar medium and a reference electrode; and
    detecting the change in potential between said electrode and said device by effecting a change in the polar state of said medium adjacent to said device.

9. A method according to claim 8, wherein a member of a specific binding pair is bound to said second hydrophobic layer and said change is a result of binding of specific binding pair members.

10. A semiconductive device comprising:
    a solid semiconductive layer having at least two areas of different dopants;
    means for detecting a change in the electrical properties of said semiconductive layer;
    an insulating oxide or nitride layer on a surface of said conductive layer;
    bound to said insulating layer, a first hydrophobic layer comprising a plurality of molecules having aliphatic chains of at least six carbon atoms, non-diffusively bound to said insulating layer;
    a second stable lamellar hydrophobic lipid layer comprising molecules having aliphatic chains of at least six carbon atoms and polar heads with said polar heads defining an electrostatically charged layer distal from said first hydrophobic layer, and wherein said individual molecules are laterally diffusible;
    wherein said first and second hydrophobic layers define a bilayer membrane.

11. A device according to claim 10, wherein said semiconductive layer is silicon and said insulative layer is of from about 10 to 500Å thick.

12. A device according to claim 11, wherein said insulative layer is of from about 10 to 100Å thick and said molecules of said second hydrophobic layer have aliphatic chains of from about 14 to 24 carbon atoms and are individual molecules.

13. A device according to claim 11, wherein said insulative layer is of from about 10 to 100Å thick and said molecules of said second hydrophobic layer have aliphatic chains of from about 14 to 24 carbon atoms and are at least in part cross-linked molecules.

14. A device according to claim 10, wherein a member of a specific binding pair is bound to said second hydrophobic layer.

15. A device according to claim 14, wherein said member of said specific binding pair is a ligand.

16. A device according to claim 14, wherein said member of said specific binding pair is a receptor.

17. A device according to claim 16, wherein said receptor is an enzyme.

18. A device according to claim 10, wherein said first hydrophobic layer is formed by reacting alkylsilyl halides with said insulating layer.

19. A method for detecting a species in an aqueous medium, wherein said species is a member of a specific binding pair, said method comprising:
    immersing in said aqueous medium a first electrode comprising a device according to claim 10 and a reference electrode, wherein a first member of said specific binding pair is bound to said second hydrophobic layer and said aqueous medium is suspected of containing a second member which is the reciprocal binding member of said first member; and
    detecting the change of potential between said electrodes as related to the amount of said second member which binds to said first member.

20. A field effect transistor transducer for detection of a change in the electrostatic environment in an aqueous medium comprising:
    a semiconductor substrate having a gate and source and drain regions spaced apart by said gate;

means for detecting an electrical signal from said source and drain regions;

an insulating layer above said gate;

a first hydrophobic layer comprising a plurality of molecules having aliphatic chains of at least six carbon atoms, non-diffusively bound to said insulating layer;

a second stable lamellar hydrophobic lipid layer comprising individual molecules having chains of at least six carbon atoms and polar heads, wherein said polar heads define a polar layer distal from said first layer, and wherein said individual molecules are laterally diffusible and non-covalently bound to said first layer;

wherein said first and second hydrophobic layers define a bilayer membrane.

21. A transducer according to claim 20, wherein said semiconductor substrate is silicon.

22. A transducer according to claim 21, wherein said molecules of said first and second layers have aliphatic chains of from 6 to 24 carbon atoms.

23. A transducer according to claim 22, wherein a member of a specific binding pair is bound to said second hydrophobic layer.

* * * * *

UNITED STATES PATENT AND TRADEMARK OFFICE
CERTIFICATE OF CORRECTION

PATENT NO. : 4,490,216                    Page 1 of 3

DATED : December 25, 1984

INVENTOR(S) : Harden M. McConnell

It is certified that error appears in the above-identified patent and that said Letters Patent is hereby corrected as shown below:

The title page should appear as shown on per attached title page.

Sheet 1 of 2 of the drawings containing Figs. 2 and 3 should be deleted to be replaced with Figs. 1-4 as shown on the attached sheet.

Signed and Sealed this

Thirtieth Day of July 1985

[SEAL]

Attest:

DONALD J. QUIGG

*Attesting Officer*      *Acting Commissioner of Patents and Trademarks*

United States Patent [19]

McConnell

[11] Patent Number: 4,490,216
[45] Date of Patent: Dec. 25, 1984

[54] LIPID MEMBRANE ELECTROANALYTICAL ELEMENTS AND METHOD OF ANALYSIS THEREWITH

[75] Inventor: Harden M. McConnell, Stanford, Calif.

[73] Assignee: Molecular Devices Corporation, Palo Alto, Calif.

[21] Appl. No.: 570,063

[22] Filed: Jan. 12, 1984

Related U.S. Application Data

[63] Continuation-in-part of Ser. No. 463,577, Feb. 3, 1983, abandoned.

[51] Int. Cl.³ .............................................. C12Q 1/00
[52] U.S. Cl. .................................. 204/1 T; 204/403; 357/25; 435/817
[58] Field of Search ............... 357/25; 324/71.6; 204/403, 1 T, 1 E; 435/817

[56] References Cited

U.S. PATENT DOCUMENTS

| | | | |
|---|---|---|---|
| 3,799,743 | 3/1974 | Alexander et al. | 422/68 |
| 3,966,580 | 6/1976 | Janata et al. | 204/403 |
| 4,020,830 | 5/1977 | Johnson et al. | 128/632 |
| 4,072,576 | 2/1978 | Arwin et al. | 435/7 |
| 4,081,334 | 3/1978 | Suzuki et al. | 204/1 T |
| 4,151,049 | 4/1979 | Janata | 204/1 T |
| 4,218,298 | 8/1980 | Shimada et al. | 204/418 |
| 4,321,123 | 3/1982 | Nakamura et al. | 204/403 |
| 4,388,165 | 6/1983 | Koshiishi et al. | 204/418 |

OTHER PUBLICATIONS

FEBS Letters, vol. 109, No. 2, pp. 252–256, Jan. 1980.
Sternberg et al., J. Colloid & Interface Science, vol. 72, No. 2, pp. 255–264, Nov. 1979.
Bergveld et al., Med. & Biol. Eng. & Compt., 17, pp. 647–654 (1979).
Bergveld et al., IEEE Trans. BMI-23, pp. 136–144, (1976).
Zemel, Surface Science, 86, pp. 322–334, (1979).
Lauks et al., IEEE Trans. Electron Devices, vol. ED-26, No. 12, pp. 1959–1964, Dec. 1979.
Bergveld, Composant Biomedical, vol. 57, pp. 451–454, (1977).
Murray, Acc. Chem. Res., 13, pp. 135–141, (1980).
Bergveld et al., Nature, vol. 273, Jun. 8, 1978.
Hafeman et al., Proc. Natl. Acad. Sci. USA, vol. 78, No. 7, pp. 4552–4556, Jul. 1981.
von Tscharner et al., Biophys. Journal, vol. 36, pp. 421–427, Nov. 1981.
Wen et al., IEEE Trans. Electron Devices, vol. ED-26, No. 12, Dec. 1979.

*Primary Examiner*—G. L. Kaplan
*Attorney, Agent, or Firm*—Bertram I. Rowland

[57] ABSTRACT

Electroanalytical elements are provided involving a polarity-sensitive layer; a first lipid layer non-diffusively bound to said polarity-sensitive layer; and, a second amphiphilic layer, with hydrophilic heads distal from said first lipid layer and defining a polar layer which interacts with said polarity-sensitive layer. The device is used in polar media to detect variations in the electrostatic interaction between the polar layer and the polarity-sensitive layer.

23 Claims, 6 Drawing Figures